United States Patent [19]
Lerner

[11] Patent Number: 5,482,052
[45] Date of Patent: Jan. 9, 1996

[54] METHOD AND APPARATUS FOR DETERMINING SENSORY FUNCTIONS

[76] Inventor: Eduard N. Lerner, Ernststraat 17, NL-1083 GP Amsterdam, Netherlands

[21] Appl. No.: 140,058

[22] PCT Filed: Apr. 29, 1991

[86] PCT No.: PCT/NL91/00071

§ 371 Date: Dec. 27, 1993

§ 102(e) Date: Dec. 27, 1993

[87] PCT Pub. No.: WO92/19154

PCT Pub. Date: Nov. 12, 1992

[51] Int. Cl.$^6$ ........................................ A61B 5/05
[52] U.S. Cl. ............................... 128/734; 128/741
[58] Field of Search ........................... 128/734, 741, 128/744–746

[56] References Cited

U.S. PATENT DOCUMENTS 3,901,215  8/1975  John .
4,088,125  5/1978  Forgione et al. ..................... 128/741

FOREIGN PATENT DOCUMENTS 0025222    3/1981  European Pat. Off. .
1557349   12/1979  United Kingdom .
WO90/14794 12/1990  WIPO .

*Primary Examiner*—Max Hindenburg
*Attorney, Agent, or Firm*—Young & Thompson

[57] ABSTRACT

A method and an instrument for measuring sensory functions (hearing vision, smell, tactile sense and pain sensitivity) of a human or an animal, whereby the sense under investigation is stimulated and the resulting change of a skin potential is recorded. Preferably, another stimulus such as an electric potential is applied, optionally several times with varying intervals and varying intensity, prior to the stimulation of the sense under investigation.

7 Claims, 1 Drawing Sheet

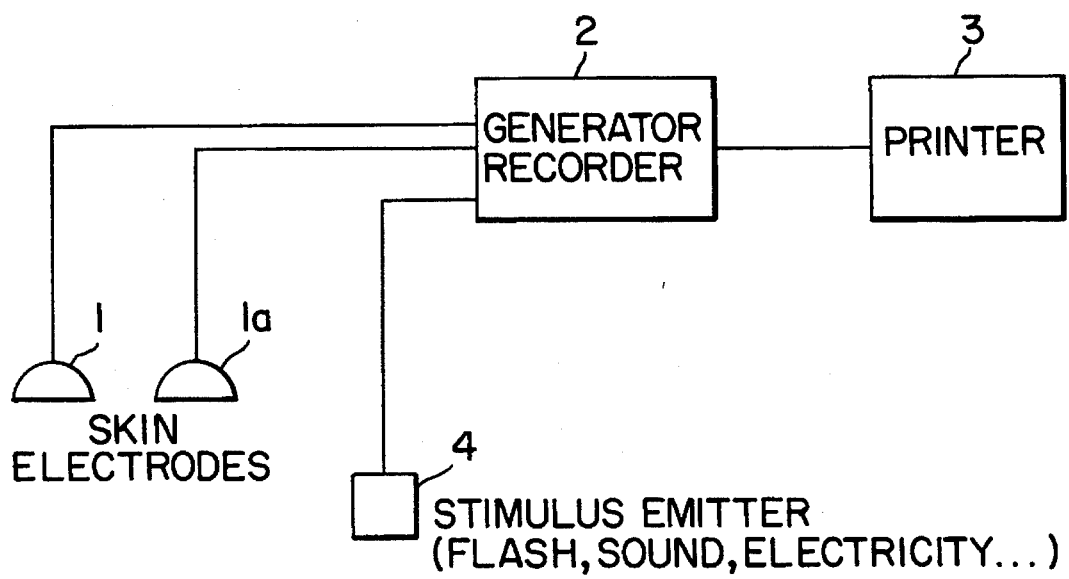

METHOD AND APPARATUS FOR DETERMINING SENSORY FUNCTIONS

BACKGROUND OF THE INVENTION

1. Field of the Invention

The present invention is in the field of medical diagnosis, in particular in the field of neurological diagnosis, and it relates to a method and a device for determining sensory functions such as hearing, sight, smell, touch and pain functions.

2. Description of the Related Art

Several methods and means for determining the degree of functioning of the senses are known. The auditory function can for example be assessed using audiometry, visual acuity by means of various tables, tactile sense by means of touch of various strength, pain sensitivity by means of a prick with a needle or with special bristles etc.

However, such methods and their variants are based on a subjective perception of the stimuli applied and on the patient's interpretation and report. The latter is a great drawback of the known methods and hampers an objective recording of the sensory perception.

An objective assessment of the functioning of the sense organs is very important in making a diagnosis, in examining children and newborn infants, in forensic medical examination and in veterinary medicine.

A method of recording skin potentials is known (I. F. Tarchanov, "The Journal of forensic psychiatry", vol 7, (1), p. 73 (1989), and others), but this method is not used for the assessment of the functional condition of the senses (vision, hearing, smell, tactile and pain sensitivity).

SUMMARY OF THE INVENTION

The purpose of the present invention is to provide a method for determining the functioning of distant senses (vision, hearing, smell) and tactile and pain sensitivity with an increased accuracy by means of electrosensometry. This method comprises recording potentials of external parts of the body such as the fingertips, at rest, whereafter auditory, visual, olfactory tactile or pain stimuli are applied and the potential change in response to the stimuli is measured and the condition of the sense under investigation is diagnosed using the result.

Although an accurate assessment of the sensory functions can be obtained in many cases using the method described above, habituation can occur upon prolonged examination in some cases, causing the results to become unreliable. This problem can be solved by the development of a conditioned reflex to an algesic stimulation with an electric current in combination with the stimulation of the sense under investigation. In the development of the conditioned reflex a specific stimulus causes a stable cutaneogalvanic reflex (CGR, skin potential reaction).

BRIEF DESCRIPTION OF THE DRAWING

FIG. 1 is a simplified schematic view of the apparatus used in carrying out the method according to the present invention.

DESCRIPTION OF THE PREFERRED EMBODIMENTS

The electro sensometry can be carried out as follows. Potentials of the phalanxes of the hand or foot or from other electroactive points are recorded. The active electrode is fixed on the palm surface, the inner side of the phalanx or another electroactive point, and the passive electrode is fixed on the back surface of the phalanx or an other, less electroactive point. Then one or more sensory stimuli (sound, light, smell, touch, prick) are applied by a stimulus emitter 4, and each time potential changes are recorded afterwards. The results of the measurement are processed. If the skin potential changes upon repeated (2–3 times) sound stimulation, this means that the sense of hearing perceives the sound stimulus. In repeated investigation it is possible to determine the threshold value of the sound perception on the basis of the intensity. If the skin potential changes upon repeated (2–3 times) light stimulation, this means that the sense of vision perceives this light stimulus. In repeated investigation it is possible again to determine the threshold value of light perception on the basis of the intensity. Using the same principle, the visual field, optionally dependent on the visual angle, can be investigated.

The results of examination are objectified by using conventional perimetry and by recording the cutaneogalvanic reaction instead of the subjective reports or in combination with such subjective reports. If the skin potential changes upon repeated (2–3 times) olfactory stimulation, this means that the sense of smell perceives the olfactory stimulus given. The limits of perception of olfactory stimuli can be determined by repeated examination on the basis of the intensity. If the skin potential changes upon repeated (2–3 times) tactile stimulation, this means that the tactile sense is preserved in the area concerned. When the examination of the tactile sense is repeated 5 to 10 times the response in the form of a potential change dies away as a result of the phenomenon of habituation. When a moderate prick with a needle or a special bristle causes a change in the skin potential, this shows that the patient has experienced a pain sensation.

In the course of any investigation of sensory functions as discussed above, a skin potential reflex may be lost due to habituation or adaptation. It has been found that this problem can be solved by using stimulation of a conditioned reflex with a second stimulus, particularly an electrical stimulus. Two small electrodes (for example 1 $cm^2$) are then connected to the palm and the back surface of a finger of the other hand or on an other area, and combinations of stimuli of the sense under investigation with an other type of stimulation are applied. This other stimulation is preferably an electric pain stimulation that may be of short duration (0.5–2 seconds), with an intensity of slightly above the threshold value, which is controlled by means of a rheostat and a voltmeter. This electric stimulation is applied 1–2 seconds after applying the specific stimulus and after for example 10–15 seconds such a combination of stimuli is repeated. After several of such combinations, for example 3–5, a stable conditioned cuteogalvanic reflex is developed and under these conditions the threshold of the sensitivity of the senses investigated is determined correctly in 93–95% of the cases. The other stimulation is preferably applied with irregular intervals and with an irregular intensity. An application in pairs of for example an electric and a visual stimulus is also advantageous.

The method according to the invention was found to be very efficacious upon investigation on the basis of measurements of the skin potential changes in various age groups (of 10–15 persons each) from the age of one month up to very old age. However, in 20 percent of the cases studied, this cuteogalvanic reflex rapidly died away, which complicated the investigation and sometimes rendered it is impossible. If, however, a conditioned reflex to a pain sensation was developed, the results of the investigation of the sensory functions turned out to be positive in more than 90 percent of the cases. The method can be used to separately examine the organs of sense, where appropriate, on both sides (right and left), optionally as a function of the direction, giving a very important contribution to the topical diagnosis of diseases and defects. The method according to the invention is applicable to living beings disposing of senses, primarily man. The method is of special interest in the examination of young children and new born infants.

Electrosensometry can also be used in veterinary medicine when examining the senses of animals, in particular pets and farm animals.

The invention also relates to a device for determining sensory functions, comprising at least one electrode (1) for measuring a skin potential and means for recording (2,3) the skin potential, and preferably also at least an electrode (1a) for administering an electric potential, as well as optionally a printer (3).

Example I

Patient B., age 28; diagnosis: healthy; hearing, vision, smell, tactile sense normal, no organic changes in the nervous system revealed.

The skin potentials were recorded on the end phalanx of one of the two forefingers using a sensitometer. Silver/silver chloride electrodes were fixed on the inner and outer surfaces of the finger and the zero elektrode was connected to the forearm. The electrodes for inducing a pain stimulation were fixed on the forefinger of the other hand. The patient was recumbent at rest in a quiet room. A sound signal in the form of a click at the ear caused a 2–3 mV deflection of the sensitometer (the background electroactivity was 8 mV). This showed that the patient perceived the signal. He confirmed this. Then a visual stimulus in the form of a light flash was applied. The sensitometer reacted also with a deflection of 3–4 mV, showing the perception of a light stimulus, which was confirmed by the patient. Investigation of the visual field was carried out using a perimeter. When a moving object entered into the visual field, a deflection of the sensitometer was observed which coincided with the patient's report. Thus, it was found that the visual field was normal. The use of a smelling substance (eau-de-cologne) also caused a deflection of the sensitometer by 2–3 mV indicating the perception of the smell by the patient. He confirmed this. Upon touching the body of the patient, a deflection of the sensitometer of 2–4 mV was recorded as well and the patient also confirmed the perception of this tactile stimulus.

The skin potential changes on the end phalanx of the toe of the same patient were examined and in response to the above mentioned stimulations 2–4 mV deflections of the sensitometer hand were obtained indicating the integrity of the senses studied. Potentials recorded in the armpit were also studied. The active electrode was fixed in the armpit and the passive one on the outer surface of the shoulder. In response to the stimuli used, the skin potential changed evidencing the perception of these stimuli by the patient.

Repeated investigation of the organs of sense (on the next day) showed that the threshold of evoking the cutaneogalvanic reflex (CGR) to light stimulation was raised significantly, and on sound stimulation hardly any CGR was evoked. Therefore a conditioned CGR was developed. At first a click at the ear was made and then a slight electrocutaneous painful irritation was applied for 1 sec. This combination was carried out 5 times with intervals of 10 sec, which led to the development of a stable conditioned reflex. In response to a minimally intensive click, CGR took place again. Thus, by means of the development of a conditioned reflex it was possible to examine all the sensory systems in the patient whereby the results were the same as the day before.

Example II

Patient K. age 33; diagnosis: thrombosis of right retina central artery. The right eye does not perceive light stimulation, in the left eye vision is intact.

The skin potentials were recorded from the end phalanx of a finger, a toe or in the armpit. The left eye was tightly closed with a bandage, the open right eye was stimulated with light flashes with short intervals. The skin potentials in the areas mentioned did not change. Upon illumination of the open left eye a distinct increase (by 2.4 mV) of the skin potential was noted. This indicates that the patient does not see with his right eye and that his left eye vision is intact.

Example III

Patient 0, age 36; diagnosis: tumour of the right cerebellopontile angle. An acute fall in hearing on the right side. With his left ear the patient hears well.

Changes in the skin potentials were studied on the end phalanx of fingers and toes and in the armpit. The left ear was closed with a tampon. On a sound signal at the right ear the skin potentials did not change, and on a sound signal at the left ear the potentials changed by 2.4 mV. This indicates an acute fall in hearing on the right sight and intact hearing in the left ear.

Example IV

Patient T, age 26; diagnosis: practically healthy, complains of complete absence of olfaction since childhood.

Skin potentials at the areas mentioned in example I in response to stimulation with odorous substances (eau de cologne, camphor) were examined. It was found that they did not change; this indicates the absence of olfactory sense.

Example V

Patient B, age 60; a year ago he had suffered disturbances in cerebral circulation in the right hemisphere with persisting left hemiparesis and left hemihypesthesia.

According to the method of the invention, the skin potentials from the forefinger phalanx of the right hand were examined. In response to a touch of the extremities on the right and on the left the amplitude of the potential changed. After the sixth touch on the left hand the amplitude of the potential did not change any more (an adaptation took place), and then a slight prick with a needle was given which did not evoke any changes in the potential either. Then, after the fourth touch on the right (healthy) hand, the potential did not change any more. A prick on the right hand however evoked a significant change (4–5 mV) in the potential. It indicates the maintenance of pain sensitivity on the right and its absence on the left.

Example VI

Patient S, age 1 month; healthy. Skin potentials on the hands and feet were examined. Electrodes were fixed on the palm and back surfaces of the hand and on the plantar and back surfaces of the foot. In response to the above-mentioned visual, auditory, olfactory and tactile stimuli (light, sound, eau-de-cologne, touch) a distinct increase by 2.4 mV in the skin potential was observed indicating the normal functioning of the senses.

Example VII

Examination of the skin potential of a dog; dog Laika, age 3 years.

Electrodes are fixed on the front and rear surfaces of the lower part of the front right paw (skin washed with soap and water, hair shaved). The presentation of visual, auditory, olfactory and tactile stimuli resulted in a distinct change of the skin potentials (by 2–3 mV). indicating that the senses function as normal.

Modifications of the invention herein disclosed will occur to a person skilled in the art and all such modifications are deemed to be within the scope of this invention as defined by the appended claims.

I claim:

1. Method for measuring sensory functions of a human or an animal comprising the steps of:
   a) applying a first stimulation of a sense of said human or animal under investigation, said first stimulation being selected from the group consisting of auditory, visual, olfactory, tactile, and pain stimuli;
   b) inducing a conditioned reflex to said first stimulation by applying a second sensory stimulation after said first stimulation of the sense so as to prevent habituation to said first stimulation;
   c) applying said first stimulation and said second stimulation repeatedly in pairs;
   d) recording a skin potential change in response to said first stimulation of the sense under investigation, said potential change being indicative of a functioning of the sense under investigation.

2. Method according to claim 1, wherein at least a skin potential on parts of limbs is recorded.

3. Method according to claim 1, wherein said second stimulation is applied as an electric stimulus.

4. Method according to the claim 1, wherein said second stimulation is applied at irregular intervals in time.

5. Method according to claim 1, wherein said second stimulation is applied with varying intensity.

6. Device for assessing sensory functions, comprising at least an electrode for measuring a skin potential and means for recording said skin potential, as well as further means for applying repeated electric potentials, electric potential intensity varying means for varying the electric potentials and electric potential interval varying means for applying the electric potentials at varying intervals in time.

7. Device according to claim 6, also comprising a manual for carrying out a diagnosis of sensory functions.

* * * * *